US009102917B2

(12) United States Patent
Tjoa et al.

(10) Patent No.: US 9,102,917 B2
(45) Date of Patent: *Aug. 11, 2015

(54) GENERATION OF DENDRITIC CELLS FROM MONOCYTIC DENDRITIC PRECURSOR CELLS WITH GM-CSF IN THE ABSENCE OF ADDITIONAL CYTOKINES

(71) Applicant: Northwest Biotherapeutics, Inc., Bethesda, MD (US)

(72) Inventors: Benjamin A. Tjoa, Seattle, WA (US); Marnix L. Bosch, Clyde Hill, WA (US)

(73) Assignee: Northwest Biotherapeutics, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/786,208

(22) Filed: Mar. 5, 2013

(65) Prior Publication Data
US 2013/0273654 A1    Oct. 17, 2013

Related U.S. Application Data

(63) Continuation of application No. 10/789,807, filed on Feb. 27, 2004, now Pat. No. 8,389,278.

(60) Provisional application No. 60/451,015, filed on Feb. 27, 2003.

(51) Int. Cl.
*C12N 5/071*     (2010.01)
*C12N 5/00*      (2006.01)
*C12N 5/0784*    (2010.01)

(52) U.S. Cl.
CPC .......... *C12N 5/0639* (2013.01); *C12N 2500/72* (2013.01); *C12N 2501/22* (2013.01); *C12N 2501/23* (2013.01); *C12N 2501/24* (2013.01)

(58) Field of Classification Search
None
See application file for complete search history.

(56) References Cited

U.S. PATENT DOCUMENTS

| 5,162,504 | A  | 11/1992 | Horoszewicz |
| 5,788,963 | A  | 8/1998  | Murphy      |
| 5,851,756 | A  | 12/1998 | Steinman    |
| 5,994,126 | A  | 11/1999 | Steinman    |
| 2002/0160430 | A1 | 10/2002 | Steinman |
| 2005/0173315 | A1 | 8/2005  | Bosch    |

FOREIGN PATENT DOCUMENTS

| EP | 0 205 387 A2 | 12/1986 |
| WO | 02/44338 A2  | 6/2002  |
| WO | 03/010292 A2 | 2/2003  |
| WO | 2004/000444 A1 | 12/2003 |

OTHER PUBLICATIONS

Araki et al., 2001, Brit. J. Heam. vol. 114: 681-689.*
Bernard, J., et al., "Adherent-Free Generation of Functional Dendritic Cells From Purified Blood Monocytes in View of Potential Clinical Use," Hematology and Cell Therapy 40(1):17-26, Feb. 1998.
Bernhard, H., et al., "Generation of Immunostimulatory Dendritic Cells From Human CD34+ Hematopoietic Progenitor Cells of the Bone Marrow and Peripheral Blood," Cancer Research 55(5):1099-1104, Mar. 1995.
Bosch, M.L., et al., "Generation of Optimal Monocyte-Derived Dendritic Cells for Immunotherapy," Journal of Investigative Dermatology [Abstract C30] 117(4):1008, Oct. 2001.
Bosch, M.L., et al., "IL-4 is Not Required for the Generation and Function of Dendritic Cells From Non-Activated Monocytes," FASEB Journal [Abstract] 17:C125, Apr. 2003.
Caux, C., et al., "GM-CSF and TNF-α Cooperate in the Generation of Dendritic Langerhans Cells," Nature 360(6401):258-261, Nov. 1992.
Chaperot, L., et al., "Differentiation of Antigen-Presenting Cells (Dendritic Cells and Macrophages) for Therapeutic Application in Patients With Lymphoma," Leukemia 14(9):1667-1677, Sep. 2000.
De Bruijn, M.L., et al., "Mechanisms of Induction of Primary Virus-Specific Cytotoxic T Lymphocyte Responses," European Journal of Immunology 22(11):3013-3020, Nov. 1992.
Dozmorov, I., and R.A. Miller, "In Vitro Production of Antigen-Specific T Cells From Unprimed Mice: Role of Dexamethasone and Anti-IL-10 Antibodies," Cellular Immunology 178(2):187-196, Jun. 1997.
Feng, Q., et al., "Purification and Biochemical Characterization of the 7E11-C5 Prostate Carcinoma-Associated Antigen," Proceedings of the American Association for Cancer Research, May 15-18, 1991, Houston, Tex., vol. 32, p. 239.
Freudenthal, P.S., and R.M. Steinman, "The Distinct Surface of Human Blood Dendritic Cells, as Observed After an Improved Isolation Method," Proceedings of the National Academy of Sciences USA (PNAS) 87(19):7698-7702, Oct. 1990.
Grey, H.M., et al., "Class I MHC-Peptide Interactions: Structural Requirements and Functional Implications," Cancer Surveys 22:37-49, 1995.

(Continued)

*Primary Examiner* — Amy Juedes
(74) *Attorney, Agent, or Firm* — Christensen O'Connor Johnson Kindness PLLC

(57) ABSTRACT

The present invention it was determined that dendritic cells could be derived from various sources including peripheral blood monocytes in the presence of only GM-CSF without other cytokines if the monocytes were not activated. By preventing activation, such as by preventing binding of the cells to the surface of the culture vessel, the monocytes do not require the presence of additional cytokines, such as IL-4 or IL-13, to prevent differentiation into a non-dendritic cell lineage. The immature DCs generated and maintained in this manner were CD14$^-$ and expressed high levels of CD1a. Upon maturation by contact with an agent such as, for example, BCG and IFNγ, the cells were determined to express surface molecules typical of mature dendritic cells purified by prior methods and cultured in the presence of GM-CSF and IL-4. The mature dendritic cells produced from monocytes without activation and cultured in GM-CSF alone are suitable for use in dendritic cell-based immunotherapy methods, such as for use in the treatment of disease, including cancer.

17 Claims, 13 Drawing Sheets

(56) References Cited

OTHER PUBLICATIONS

Horoszewicz, J.S., et al., "The LNCaP Cell Line: A New Model for Studies on Human Prostatic Carcinoma," Progress in Clinical and Biological Research 37:115-132, 1980.

Inaba, K., et al., "Direct Activation of CD8• Cytotoxic T Lymphocytes by Dendritic Cells," Journal of Experimental Medicine 166(1):182-194, Jul. 1987.

Kasinrerk, W., et al., "CD1 Molecule Expression on Human Monocytes Induced by Granulocyte-Macrophage Colony-Stimulating Factor," Journal of Immunology 150(2):579-584, Jan. 1993.

Lewalle, P., et al., "Freezing of Dendritic Cells, Generated From Cryopreserved Leukaphereses, Does Not Influence Their Ability to Induce Antigen-Specific Immune Responses or Functionally React to Maturation Stimuli," Journal of Immunological Methods 240(1-2):69-78, Jun. 2000.

Lutz, M.B., et al., "An Advanced Culture Method for Generating Large Quantities of Highly Pure Dendritic Cells From Mouse Bone Marrow," Journal of Immunological Methods 223(1):77-92, Feb. 1999.

Lutz, M.B., et al., "Immature Dendritic Cells Generated with Low Doses of GM-CSF in the Absence of IL-4 are Maturation Resistant and Prolong Allograft Survival In Vivo," European Journal of Immunology 30(7):1813-1822, Jul. 2000.

Macatonia, S.E., et al., "Primary Stimulation by Dendritic Cells Induces Antiviral Proliferative and Cytotoxic T Cell Responses in Vitro," Journal of Experimental Medicine 169(4):1255-1264, Apr. 1989.

Macatonia, S.E., et al., "Suppression of Immune Responses by Dendritic Cells Infected With HIV," Immunology 67(3):285-289, Jul. 1989.

Maffei, A., et al., "A Novel Closed System Utilizing Styrene Copolymer Bead Adherence for the Production of Human Dendritic Cells," Transfusion 40(11):1419-1420, Nov. 2000.

Markowicz, S., and E.G. Engleman, "Granulocyte-Macrophage Colony-Stimulating Factor Promotes Differentiation and Survival of Human Peripheral Blood Dendritic Cells in Vitro," Journal of Clinical Investigation 85(3):955-961, Mar. 1990.

Matera, L., et al., "Individual and Combined Effect of Granulocyte-Macrophage Colony-Stimulating Factor and Prolactin on Maturation of Dendritic Cells From Blood Monocytes Under Serum-Free Conditions," Immunology 100(1):29-36, May 2000.

O'Doherty, U., et al., "Dendritic Cells Freshly Isolated From Human Blood Express CD4 and Mature Into Typical Immunostimulatory Dendritic Cells After Culture in Monocyte-Conditioned Medium," Journal of Experimental Medicine 178(3):1067-1076, Sep. 1993.

Riddell, S.R., et al., "Restoration of Viral Immunity in Immunodeficient Humans by the Adoptive Transfer of T Cell Clones," Science 257(5067):238-241, Jul. 1992.

Sallusto, F., and A. Lanzavecchia, "Efficient Presentation of Soluble Antigen by Cultured Human Dendritic Cells is Maintained by Granulocyte/Macrophage Colony-Stimulating Factor Plus Interleukin 4 and Downregulated by Tumor Necrosis Factor α," Journal of Experimental Medicine 179(4):1109-1118, Apr. 1994.

Steel, C., and T.B. Nutman, "Helminth Antigens Selectively Differentiate Unsensitized CD45RA•CD4• Human T Cells In Vitro," Journal of Immunology 160(1):351-360, Jan. 1998.

Steinman, R.M., "The Dendritic Cell System and its Role in Immunogenicity," Annual Review of Immunology 9:271-296, Apr. 1991.

Stevenson, H.C., et al., "Characterization of Purified Cryopreserved Human Monocyte Function in Assays of Superoxide Production, Accessory Cell Function, Chemotaxis, and in Fluorescent Cell Sorter Analysis," Journal of Leukocyte Biology 36(4):521-531, Oct. 1984.

Strominger, J.L., et al., "Regulation of Dendritic Cell Subsets by NKT Cells," Comptes Rendus Biologies 326(10-11):1045-1048, Oct.-Nov. 2003.

Tao, X., et al., "Induction of IL-4-Producing CD4•T Cells by Antigenic Peptides Altered for TCR Binding," Journal of Immunology 158(9):4237-4244, May 1997.

Young, J.W., and R.M. Steinman, "Dendritic Cells Stimulate Primary Human Cytolytic Lymphocyte Responses in the Absence of CD4•Helper T Cells," Journal of Experimental Medicine 171(4):1315-1332, Apr. 1990.

* cited by examiner

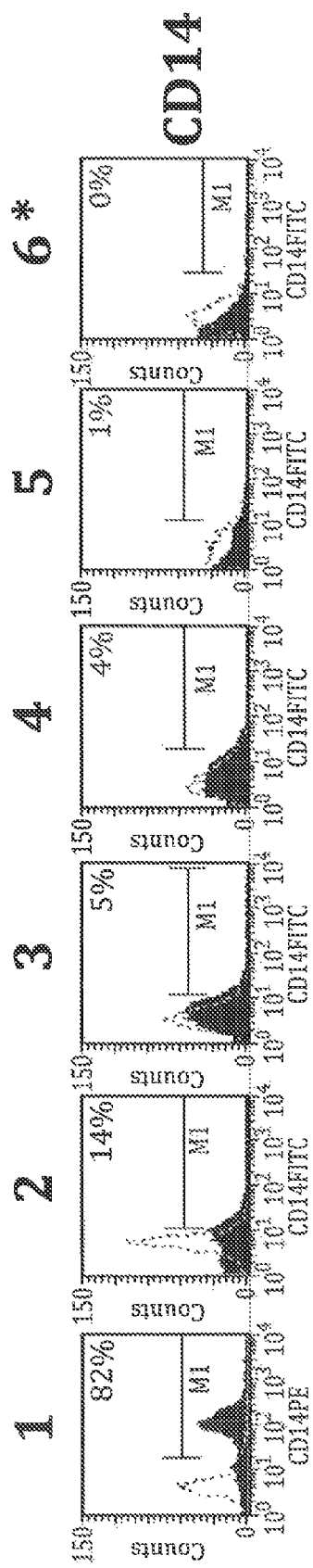
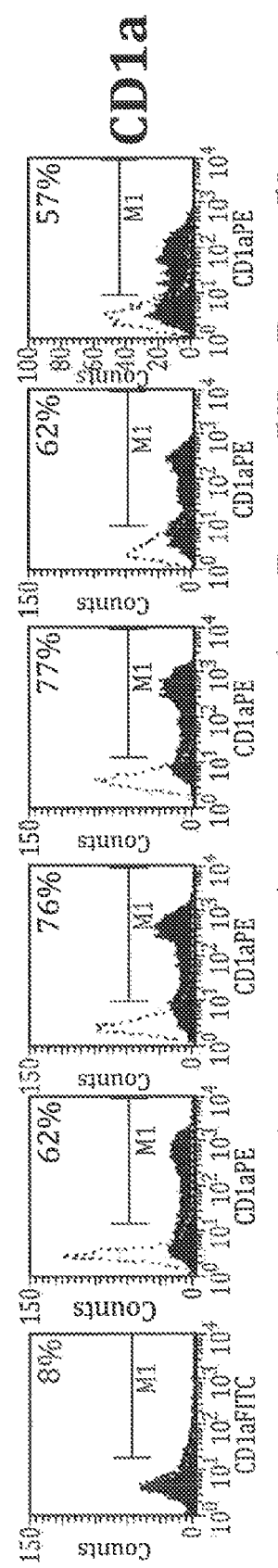
Figure 5A–5F (CD14); Figure 5G–5L (CD1a). Number of days in culture.

GENERATION OF DENDRITIC CELLS FROM MONOCYTIC DENDRITIC PRECURSOR CELLS WITH GM-CSF IN THE ABSENCE OF ADDITIONAL CYTOKINES

This application is a continuation of U.S. patent application Ser. No. 10/789,807, filed Feb. 27, 2004, which claims the benefit of U.S. Provisional Patent Application No. 60/451,015, filed Feb. 27, 2003, the disclosures of which are incorporated herein in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 40795_ST25.txt. The text file is 2 KB, was created on Jul. 14, 2014, and is being submitted via EFS-Web with the filing of the specification.

BACKGROUND OF THE INVENTION

Antigen presenting cells (APC) are important in eliciting an effective immune response. APC not only present antigens to T cells with antigen-specific receptors, but also provide the signals necessary for T cell activation. Such signals remain incompletely defined, but are known to involve a variety of cell surface molecules as well as cytokines or growth factors. The factors necessary for the activation of naive or unprimed T cells may be different from those required for the re-activation of previously primed memory T cells. Although monocytes and B cells have been shown to be competent APC, their antigen presenting capacities appear to be limited to the re-activation of previously sensitized T cells. Hence, they are not capable of directly activating functionally naive or unprimed T cell populations. On the other hand, dendritic cells are capable of both activating naive and previously primed T cells.

Dendritic cells are a heterogeneous cell population with a distinctive morphology and a widespread tissue distribution, including blood. (See, e.g., Steinman, *Ann. Rev. Immunol.* 9:271-96 (1991)). The cell surface of dendritic cells is unusual, with characteristic veil-like projections. Mature dendritic cells are generally identified as $CD3^-$, $CD11c^+$, $CD19^-$, $CD83^+$, $CD86^+$ and HLA-$DR^+$.

Dendritic cells process and present antigens, and stimulate responses from naive and unprimed T cells and memory T cells. In particular, dendritic cells have a high capacity for sensitizing MHC-restricted T cells and are very effective at presenting antigens to T cells, both self-antigens during T cell development and tolerance, and foreign antigens during an immune response. In addition to their role in antigen presentation, dendritic cells also directly communicate with non-lymph tissue and survey non-lymph tissue for an injury signal (e.g., ischemia, infection, or inflammation) or tumor growth. Once signaled, dendritic cells initiate an immune response by releasing cytokines that stimulate activity of lymphocytes and monocytes.

Due to their effectiveness at antigen presentation, there is growing interest in using dendritic cells as an immunostimulatory agent, both in vivo and ex vivo. The use of isolated dendritic cells as immunostimulatory agents has been limited, however, due to the low frequency of dendritic cells in peripheral blood and the low purity of dendritic cells isolated by prior methods. In particular, the frequency of dendritic cells in human peripheral blood has been estimated at about 0.1% of the white cells. Similarly, there is limited accessibility of dendritic cells from other tissues, such as lymphoid organs. The low frequency of dendritic cells has increased interest in isolating cell population enriched in dendritic cell precursors, and culturing these precursors ex vivo or in vitro to obtain enriched populations of immature or mature dendritic cells. Because the characteristics of dendritic cell precursors remain incompletely defined, methods typically used for isolating dendritic cell precursors do not result in purified fractions of the desired precursors, but instead generally produce mixed populations of leukocytes enriched in dendritic cell precursors. Several cell types have been identified as having the potential to function as dendritic cell precursors. Blood-derived CD14+ monocytes, especially those that express on their surface the receptor for the growth factor granulocyte-monocyte colony stimulating factor (GM-CSF) are known dendritic cell precursors. Other blood-derived dendritic cell precursors can be isolated by first removing monocytes and other "non-dendritic cell precursors" (See, e.g., U.S. Pat. Nos. 5,994,126 and 5,851,756.). Yet other known dendritic cell precursors include bone marrow-derived cells that express the CD34 cell surface marker.

Cell populations enriched in dendritic cell precursors have been obtained by various methods, such as, for example, density gradient separation, fluorescence activated cell sorting, immunological cell separation techniques, e.g., panning, complement lysis, rosetting, magnetic cell separation techniques, nylon wool separation, and combinations of such methods. (See, e.g., O'Doherty et al., *J. Exp. Med.* 178:1067.76 (1993); Young and Steinman, *J. Exp. Med.* 171:1315-32 (1990); Freudenthal and Steinman, *Proc. Natl. Acad. Sci. USA* 87:7698-702 (1990); Macatonia et al., *Immunol.* 67:285-89 (1989); Markowicz and Engleman, *J. Clin. Invest.* 85:955-61 (1990) all incorporated herein by reference in their entirety). Methods for immuno-selecting dendritic cells include, for example, using antibodies to cell surface markers associated with dendritic cell precursors, such as anti-CD34 and/or anti-CD14 antibodies coupled to a substrate. (See, e.g., Bernhard et al., *Cancer Res.* 55:1099-104 (1995); Caux et. al., *Nature* 360:258-61 (1992)).

In one typical example method, leukocytes are isolated by a leukapheresis procedure. Additional methods are typically used for further purification to enrich for cell fractions thought to contain dendritic cells and/or dendritic cell precursors. Similarly, methods such as differential centrifugation (e.g., isolation of a buffy coat), panning with monoclonal antibodies specific for certain cell surface proteins (e.g., positive and negative selection), and filtration also produce a crude mixture of leukocytes containing dendritic cell precursors.

Another reported method for isolating proliferating dendritic cell precursors is to use a commercially treated plastic substrate (e.g., beads or magnetic beads) to selectively remove adherent monocytes and other "non-dendritic cell precursors." (See, e.g., U.S. Pat. Nos. 5,994,126 and 5,851,756). The adherent monocytes and non-dendritic cell precursors are discarded while the non-adherent cells are retained for ex vivo culture and maturation. In another method, apheresis cells were cultured in plastic culture bags to which plastic, i.e., polystyrene or styrene, microcarrier beads were added to increase the surface area of the bag. The cells were cultured for a sufficient period of time for cells to adhere to the beads and the non-adherent cells were washed from the bag. (Maffei, et al., *Transfusion* 40:1419-1420 (2000); WO 02/44338, incorporated herein by reference).

Subsequent to essentially all of the reported methods for the preparation of a cell population enriched for dendritic cell precursors, the cell populations are typically cultured ex vivo or in vitro for differentiation of the dendritic cell precursors or maintenance, and/or expansion of the dendritic cells. Briefly, ex vivo differentiation of monocytic dendritic cell precursors has involved culturing the mixed cell populations enriched for dendritic cell precursors in the presence of combinations of cellular growth factors, such as cytokines. For example, monocytic dendritic cell precursors require granulocyte/monocyte colony-stimulating factor (GM-CSF) in combination with at least one other cytokine selected from, for example, either Interleukin 4 (IL-4), Interleukin 15 (IL-15), Interleukin 13 (IL-13), interferon α (IFN-α), and the like, to differentiate the cells into an optimal state for antigen uptake, processing, and/or presentation. The numbers of dendritic cells from non-monocytic dendritic cell precursors, such as those obtained by removal of monocytes and other non-dendritic precursor cells (adsorption to a plastic surface) or selection for $CD34^+$ cells, have also been expanded by culture in the presence of certain cytokines. Either GM-CSF alone or a combination of GM-CSF and IL-4 have been used in methods to produce dendritic cell populations from such proliferating dendritic cell precursors for therapeutic use.

The effectiveness of such ex vivo differentiation, maintenance and/or expansion has been limited, however, by the quality of the starting population enriched in dendritic cells and dendritic cell precursors. Under some culture conditions, populations of dendritic cells and dendritic cell precursors that are heavily contaminated with neutrophils, macrophages and lymphocytes, or combinations thereof, can be overtaken by the latter cells, resulting in a poor yield of dendritic cells. Culture of dendritic cells containing large numbers of neutrophils, macrophages and lymphocytes, or combinations thereof, are less suitable for use as immunostimulatory preparations.

Immature or mature dendritic cells, once obtained, typically have been exposed to a target antigen(s) and maturation agents to provide activated mature dendritic cells. In general, the antigen has been added to a cell population enriched for immature or mature dendritic cells under suitable culture conditions. In the case of immature dendritic cells, the cells are then allowed sufficient time to take up and process the antigen, and express antigenic peptides on the cell surface in association with either MHC class I or class II markers. Antigen can be presented to immature dendritic cells on the surface of cells, in purified form, in a semi-purified form, such as an isolated protein or fusion protein (e.g., a GM-CSF-antigen fusion protein), as a membrane lysate, as a liposome-protein complex, and other methods. In addition, as mature dendritic cells are not capable of taking up and processing antigen, antigenic peptides that bind to MHC class I or MHC class II molecules can be added to mature dendritic cells for presentation.

Once activated dendritic cells have been obtained, they have been administered to a patient to stimulate an immune response. Activated dendritic cells can be administered to a patient by bolus injection, by continuous infusion, sustained release from implants, or other suitable techniques known in the art. The activated dendritic cells also can be co-administered with physiologically acceptable carriers, excipients, buffers and/or diluents. Further, activated dendritic cells can be used to activate T cells, e.g., cytotoxic T cells, ex vivo using methods well known to the skilled artisan. The antigen specific cytotoxic T cells can then be administered to a patient to treat, for example, a growing tumor, or a bacterial or viral infection. These compositions can be used by themselves or as an adjuvant to other therapies, such as, for example, surgical resection, chemotherapy, radiation therapy, and combinations thereof, as well as other therapeutic modalities appropriate for the condition being treated.

The present invention has found that contrary to prior methods monocytic dendritic cell precursors can be differentiated into immature dendritic cells and maintained in a suitable condition that is fully competent to process and present antigen in the presence of GM-CSF alone without additional cytokines. The methods comprise providing a cell population comprising dendritic cell precursors which have not been activated and culturing the cells in vitro or ex vivo in a dendritic cell culture medium that has been supplemented with GM-CSF without any additional cytokines. Methods typically used to enrich cell populations for dendritic cell precursors can activate the precursor cells initiating terminal differentiation of the cells into, for example, macrophage. The addition of other cytokines, for example IL-4, IL-13, IL-15, or TNF-α, countered the effects of the isolation associated activation of the cells. The practice of the methods of the present invention provides for a simple and more cost effective method to obtain and maintain immature dendritic cells in a state optimized for the uptake, processing and presentation of a selected antigen.

BRIEF SUMMARY OF THE INVENTION

The present invention provides a method for differentiating and maintaining immature dendritic cells ex vivo or in vitro in a state optimized for the uptake, processing and presentation of a selected antigen. The method comprises providing a cell population comprising non-activated monocytic dendritic cell precursors i.e., monocytes that express the GM-CSF receptor on their surface, and other such dendritic cell precursors, and contacting the non-activated dendritic cell precursors with a dendritic cell culture media supplemented with granulocyte-macrophage colony stimulating factor in the absence of additional cytokines. Contrary to prior methods the additional cytokines are not required for the generation of dendritic cells from isolated non-activated monocytic dendritic cell precursors.

Activation of the monocytic dendritic precursor cells can be prevented by, for example, inhibiting or blocking the adhesion of the precursor cells to a solid surface the cells would contact during a typical isolation and/or enrichment process or during cell culture. The solid surface can be a culture vessel, such as a cell culture flask, bottle or bag, used to obtain or maintain the cells ex vivo or in vitro. The solid surface can also be any surface of a vessel or device used in the preparation of cell population enriched for the dendritic cell precursors, e.g., a filter surface; a bead used in purification, such as a magnetic, glass or plastic bead; tubing, culture vessel, and the like. Inhibition of the adhesion of the non-activated monocytic dendritic cell precursors can be by the addition of a high concentration of an animal or human protein to the cell culture or isolation medium. A high concentration of animal or human protein as used herein comprises about 1 to about 10% w/v of the protein. The animal protein can comprise an albumin, serum, plasma, gelatin, poly-amino acid, and the like, as long as they do not themselves activate the cells. Activation of the monocytic dendritic precursor cells can also be blocked or inhibited by the addition of a metal chelator to the cell culture and/or isolation medium. The metal chelator can comprise EDTA, EGTA, and the like. The addition of these dendritic cell agents is believed to minimize the activation of the precursor cells by reducing the concentration of divalent cationic metals in the culture media.

Activation of the monocytic dendritic precursor cells can also be prevented or inhibited by isolation or enrichment and culturing of the dendritic precursor cells in a low cellular avidity culture vessel. The low cellular avidity culture vessels typically comprise materials such as polypropylene, Teflon®, PFTE, and the like. As with adding the animal or human protein reducing or blocking adhesion of the dendritic precursor cell to the solid surface prevents activation of the cells and allows for the differentiation and maintenance of the cells into immature dendritic cells in the presence of dendritic cell culture media supplemented with GM-CSF without any additional cytokines. Performing the isolation of the precursor cells at temperatures below about 37° C., such as room temperature, further reduces the proportion of monocytic dendritic precursor cells that under go activation in the cell population. The methods of the present invention can comprise the combination of any or all of these agents, materials, and/or conditions. In one particular embodiment of the invention the dendritic cell culture medium is serum free and an animal protein, such as serum albumin, is added to decrease the avidity of the dendritic cell precursors for the surface of the culture vessel to prevent and/or reduce activation of the monocytic dendritic precursor cells.

Typically the cell populations that comprise monocytic dendritic precursor cells are obtained from peripheral blood, a leukapheresis product, an apheresis product, cord blood, spleen, lymph node, thymus, or bone marrow. The cell populations can be cryopreserved prior to and subsequent to practice of the methods of the present invention. Further, the cell population can be further enriched for monocytic precursor cells by tangential flow filtration, antibody panning, differential centrifugation, and the like. When the cell population is further enriched by tangential flow filtration the filter typically comprises a 5.5 micron pore, the recirculation rate is about 1400 ml/min, the filtration rate is approximately 15 to about 21 ml/min, typically 17 ml/min, and the filtration time is about 60 to about 90 min. (See, for example, WO2004/000444, published on Dec. 31, 2003, incorporated herein by reference).

Immature dendritic cells that have been obtained by the methods of the present invention can be contacted with a selected antigen of interest for a time period sufficient for uptake and processing of the antigen. Once processed the antigen is presented on the surface of the dendritic cells. Further, the immature dendritic cells can be contacted with a dendritic cell maturation agent either prior to, simultaneously with, or subsequent to contact with the antigen of interest. The dendritic cell maturation agent can comprise Bacillus Calmette-Guerin (BCG), lipopolysaccharide (LPS), tumor necrosis factor α (TNF-α), interferon gamma (IFN-γ), or combinations thereof. In particular embodiments of the present invention the dendritic cell maturation agent is a combination of inactivated BCG and IFN-γ. Selected antigens useful in the methods of the present invention include, but are not limited to a tumor specific antigen, a tumor associated antigen, a viral antigen, a bacterial antigen, tumor cells, nucleic acid obtained from tumor cells, bacterial cells, viral particles, recombinant cells expressing an antigen, a cell lysate, a membrane preparation, a recombinantly produced antigen, a peptide derived from the antigen of interest, or an isolated antigen of interest. At any stage, including subsequent to contact with the selected antigen, uptake, processing and maturation of the dendritic cells, the cells can be cryopreserved for later use.

BRIEF DESCRIPTION OF THE DRAWINGS

FIG. 2 depicts the measurement of expression of CD1a and CD14 as monocytes differentiate in to dendritic cells (DC) following in vitro culture in the absence of IL-4. Differentiation is indicated by the reciprocal expression of the markers CD1a and CD14 on "live" CD11c$^+$ cells.

FIG. 5 depicts the kinetics of in vitro dendritic cell differentiation of non-activated monocytes in cell culture media supplemented with GM-CSF alone as determined by the expression of CD1a and CD14.

FIG. 6A depicts the percentage of cells that were CD1a positive. FIG. 6B depicts the percentage of cells that were CD83 positive. FIG. 6C depicts the relative level of expression (mfi) of CD80. FIG. 6D depicts the relative level of expression (mfi) of CD86. FIG. 6E depicts the relative level of expression (mfi) of HLA-DR.

FIG. 7A depicts the antigen specific cytotoxic T cell analysis for cells isolated from donor P016 and FIG. 7B is a similar analysis for donor P052.

FIG. 8A depicts the percentage of CD11c$^+$ cells that co-express specific markers on monocytes and on day 5 DC. FIG. 8B depicts the relative expression of phenotypic markers. Data are shown for independent cultures from two different donors designated 63665 and 63666 after electronic gating on cells of the monocyte lineage (CD11c$^+$) for (i) subsets and (ii) relative expression as measured by mean fluorescence intensity (mfi). Background staining observed with the relevant isotype control antibodies have been subtracted.

DETAILED DESCRIPTION OF THE INVENTION

Figure 1:
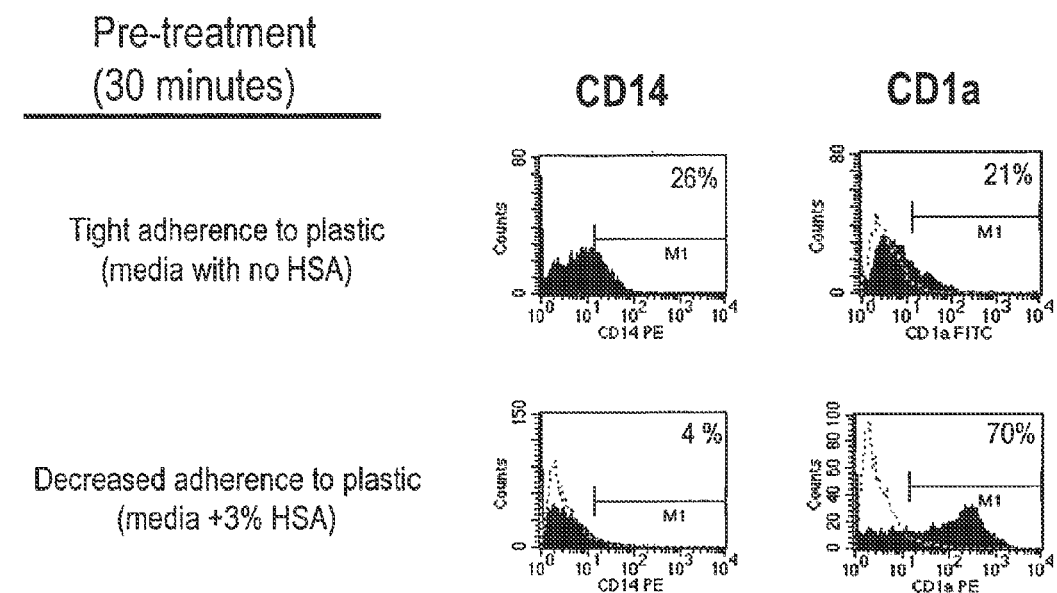
FIG. 1 depicts histograms of the surface expression of CD14 and CD1a on dendritic cells to evaluate the in vitro differentiation of monocytic dendritic cell precursors into CD1a$^+$ dendritic cells in the presence of GM-CSF alone without additional cytokines and in the presence of a blocking agent (3% human serum albumin; HSA) that prevents tight binding to the surface of the cell culture container.

The present invention provides methods for the differentiation of monocytic dendritic cell precursors into immature dendritic cells (DC). The monocytic dendritic cell precursors which have not been activated can be contacted with a dendritic cell culture media supplemented with GM-CSF as the only cytokine to induce differentiation and maintenance of the cells as immature dendritic cells. Methods which only require the addition of a single cytokine are less expensive to use and are more efficient than those used previously that require the addition of other cytokines to prevent differentiation of the monocytic dendritic cells into other cell types including, for example, macrophage, and the like.

The immature dendritic cells produced by the methods of the present invention are phenotypically and functionally similar to those produced by prior methods that use more complex culture conditions and can subsequently be contacted with a dendritic cell maturation factor, such as BCG and IFNγ, and optionally with a predetermined antigen under suitable maturation conditions. Antigen can be contacted with the immature dendritic cells of the invention either during or prior to maturation.

Monocytic Dendritic Cell Precursors and Immature Dendritic Cells

Monocytic dendritic cell precursors as used herein comprise monocytes that have the GM-CSF receptor on their surface and other myeloid precursor cells that are responsive to GM-CSF. The cells can be obtained from any tissue where they reside, particularly lymphoid tissues such as the spleen, bone marrow, lymph nodes and thymus. Monocytic dendritic cell precursors also can be isolated from the circulatory system. Peripheral blood is a readily accessible source of monocytic dendritic cell precursors. Umbilical cord blood is another source of monocytic dendritic cell precursors. Monocytic dendritic cell precursors can be isolated from a variety of organisms in which an immune response can be elicited. Such organisms include, for example, humans, and non-human animals, such as, primates, mammals (including dogs, cats, mice, and rats), birds (including chickens), as well as transgenic species thereof.

In certain embodiments, the monocytic dendritic cell precursors and/or immature dendritic cells can be isolated from a healthy subject or from a subject in need of immunostimulation, such as, for example, a cancer patient or other subject for whom cellular immunostimulation can be beneficial or desired (i.e., a subject having a bacterial, viral or parasitic infection, and the like). Monocytic dendritic cell precursors and/or immature dendritic cells also can be obtained from an HLA-matched healthy individual for conversion to immature dendritic cells, maturation, activation and administration to an HLA-matched subject in need of immunostimulation.

Methods for isolating non-activated monocytic dendritic cell precursors and immature dendritic cells from the various sources provided above, including blood and bone marrow, can be accomplished in a number of ways. Typically, a cell population is collected from the individual and enriched for the non-activated monocytic dendritic cell precursors. For example, a mixed population of cells comprising the non-activated monocytic dendritic cell precursors can be obtained from peripheral blood by leukapheresis, apheresis, density centrifugation, differential lysis, filtration, antibody panning, or preparation of a buffy coat. The method selected must not activate the monocytic dendritic cell precursors. For example, if antibody panning is selected to enrich the cell population for precursors the antibodies selected must not activate the cells, e.g., through the induction of the influx of calcium ions which can result as a consequence of crosslinking the molecules on the surface to which the antibodies bind. Typically, when antibody panning, antibodies are used that eliminate macrophage, B cells, Natural Killer cells, T cells and the like. Antibodies can also be used to positively select for monocyte like cells that express CD14.

In one embodiment of the present invention the non-activated monocytic dendritic cell precursors are prepared by preventing the tight adherence of the population of cells comprising the monocytic dendritic cell precursors to a cell culture vessel. Tight adherence can be prevented by, for example, adding a blocking agent to the culture media used to maintain the dendritic cell precursors in vitro or ex vivo. Such blocking agents can include high concentrations of protein, including for example and not as a limitation, an animal or human protein, such as albumins, serum, plasma, gelatin, polyamino acids, and the like. In particular, albumins from bovine or human sources are typically used. Typically, a concentration of about 1% to about 10% w/v blocking agent is used. In particular, human serum albumin (HSA) can be used at a concentration of about 1%, 2% or up to about 5% or more. It should be noted that blocking agents must be selected that do not themselves activate the cells. The culture media can be any media typically used for the culture of monocytic dendritic cell precursors including those that do not require serum.

In another embodiment of the invention, a metal chelator can be added to the culture media to further prevent or reduce the activation of the monocytic dendritic cells by chelating divalent cations, including for example, but not limitation, calcium ions. The use of low adherence or low-binding culture vessels can also reduce the avidity of attachment or binding of the dendritic cell precursors to prevent the cells from being activated. Particularly preferred low binding materials include, for example, but are not limited to, polypropylene, Teflon®, PFTE, and the like. The metal chelator can be used in combination with the blocking agents described above.

Monocytic dendritic cell precursors and immature dendritic cells can also be prepared in a closed, aseptic system. As used herein, the terms "closed, aseptic system" or "closed system" refer to a system in which exposure to non-sterile, ambient, or circulating air or other non-sterile conditions is minimized or eliminated. Closed systems for isolating dendritic cell precursors and immature dendritic cells generally exclude density gradient centrifugation in open top tubes, open air transfer of cells, culture of cells in tissue culture plates or unsealed flasks, and the like. In a typical embodiment, the closed system allows aseptic transfer of the dendritic cell precursors and immature dendritic cells from an initial collection vessel to a sealable tissue culture vessel without exposure to non-sterile air.

In certain embodiments, non-activated monocytic dendritic cell precursors are isolated by partial adherence to a monocyte-binding substrate, as disclosed in WO03/010292, the disclosure of which is incorporated by reference herein. For example, a population of leukocytes (e.g., isolated by leukopheresis) can be contacted with a monocytic dendritic cell precursor adhering substrate, e.g., a glass coated microcarrier bead, in the presence of a blocking agent that prevents non-specific binding as well as reduces the binding avidity of the monocytic dendritic cell precursor cells. When the population of leukocytes is contacted with the substrate, the monocytic dendritic cell precursors in the leukocyte population preferentially loosely adhere to the substrate. Other leukocytes (including other potential dendritic cell precursors) e.g., proliferating dendritic cell precursors, and the like exhibit reduced binding affinity to the substrate, thereby allowing a subset of the monocytic dendritic cell precursors to be preferentially enriched on the surface of the substrate. Loose adhesion does not activate the monocytic dendritic cell precursors. Subsequent to cell binding and elution of non-adherent cells, the subset of monocytic dendritic cell precursors are eluted from the substrate by a buffered salt solution that can be supplemented with a non-toxic chelating agent. By "non-toxic chelating agent" is intended those chelating agents that do not substantially reduce the viability of the monocytic dendritic cell precursors, for example but not limitation, EDTA, EGTA, and the like.

Suitable substrates include, for example, those having a large surface area to volume ratio, such as glass beads or a glass coated microcarrier. Such substrates can be, for example, a particulate or fibrous substrate. Suitable particulate substrates include, for example, glass particles, glass-coated plastic particles, glass-coated polystyrene particles, and other beads suitable for protein absorption. Suitable fibrous substrates include glass or glass coated microcapillary tubes and microvillous membrane. The particulate or fibrous substrate usually allows the adhered monocytic dendritic cell precursors to be eluted without substantially reducing the viability of the adhered cells. A particulate or fibrous substrate can be substantially non-porous to facilitate elution of monocytic dendritic cell precursors or dendritic cells from the substrate. A "substantially non-porous" substrate is a substrate in which at least a majority of pores present in the substrate are smaller than the cells to minimize entrapping cells in the substrate.

Adherence of the monocytic dendritic cell precursors to the substrate without activation can optionally be modulated by the addition of binding media. Suitable binding media include monocytic dendritic cell precursor culture media (e.g., AIM-V®, RPMI 1640, DMEM, X-VIVO 15®, and the like) supplemented, individually or in any combination, with for example, cytokines (e.g., Granulocyte/Macrophage Colony Stimulating Factor (GM-CSF), blood plasma, serum (e.g., human serum, such as autologous or allogeneic sera), purified proteins, such as serum albumin, divalent cations (e.g., calcium and/or magnesium ions) and other molecules that aid in the specific adherence of monocytic dendritic cell precursors to the substrate, or that prevent adherence of non-monocytic dendritic cell precursors to the substrate. In certain embodiments, the blood plasma or serum can be heat-inactivated. The heat-inactivated plasma can be autologous or heterologous to the leukocytes.

In another method for enriching a cell population for monocytic dendritic cell precursors from a sample of blood constituents provides for tangential flow filtration of the leukocytes from cellular debris, red blood cells and other cells and particles in a blood sample. A description of the device and its use is described in WO02004/000444, incorporated herein by reference in its entirety. The method comprises (1) introducing the blood sample into a tangential flow filtration (TFF) unit, the TFF unit comprising a cross-flow chamber, a filtrate chamber, and a filter in fluid communication with the cross-flow chamber and the filtrate chamber, the filter having a pore size of about 1 to about 10 microns, typically about 5.5 microns; (2) recirculation of the sample through the TFF unit at a predetermined input rate, typically about 1400 ml/min, and a predetermined filtration rate, typically about 15 to about 21 ml/min, more typically about 17 ml/min, the predetermined input rate at least five times the predetermined filtration rate; wherein the predetermined filtration rate is less than the unopposed filtration rate for the filter; and (3) isolating a cell population enriched for leukocytes. Typically the filtration time is about 60 to about 90 minutes. The method can result in an enriched cell population that is substantially free of non-leukocyte blood constituents including plasma, platelets and erythrocytes. The enriched cell population produced by this method can comprise at least about 50% monocytic dendritic cell precursors and preferentially at least about 70% monocytic dendritic cell precursors that have not been activated. The method can further comprise the collecting of blood from a subject and preparing the sample from the blood by leukapheresis, density centrifugation, differential lysis, filtration, or preparation of a buffy coat prior to tangential flow filtration. Performing the TFF purification of the monocytic DC precursors at room temperature, or below (i.e., below 37° C.) further aids in reducing the activation of the cells.

Cell populations enriched for non-activated monocytic dendritic cell precursors are cultured ex vivo or in vitro for differentiation, maturation and/or expansion. (As used herein, isolated immature dendritic cells, dendritic cell precursors, T cells, and other cells, refers to cells that, by human hand, exist apart from their native environment, and are therefore not a product of nature. Isolated cells can exist in purified form, in semi-purified form, or in a non-native environment.) Briefly, ex vivo differentiation typically involves culturing the non-activated dendritic cell precursors, or populations of cell comprising non-activated dendritic cell precursors, in the presence of one or more differentiation agents. In particular, the differentiation agent in the present invention is granulocyte-macrophage colony stimulating factor (GM-CSF) used alone without other added cytokines, particularly without the use of Interleukin 4 (IL-4). In certain embodiments, the non-activated monocytic dendritic cell precursors are differentiated to form monocyte-derived immature dendritic cells capable of inducing the activation and proliferation of a substantial number of T cells in a population of peripheral blood mononuclear cells.

The dendritic cell precursors can be differentiated and maintained as immature dendritic cell precursors in suitable culture conditions. Suitable tissue culture media include AIM-V®, RPMI 1640, DMEM, X-VIVO 15®, and the like supplemented with GM-CSF. The tissue culture media can be supplemented with serum, amino acids, vitamins, divalent cations, and the like, to promote differentiation of the cells into dendritic cells. In certain embodiments, the dendritic cell precursors can be cultured in a serum-free media. Such culture conditions can optionally exclude any animal-derived products. Typically, GM-CSF is added to the culture medium at a concentration of about 100 to about 1000 units/ml, or typically 500 units/ml of GM-CSF. Dendritic cell precursors, when differentiated to form immature dendritic cells demonstrate a typical expression pattern of cell surface proteins seen for immature monocytic dendritic cells, e.g., the cells are typically $CD14^-$ and $CD11c^+$, $CD83^-$ and express low levels of CD86. In addition, the immature dendritic cells are able to capture soluble antigens via specialized uptake mechanisms.

The immature dendritic cells can be matured to form mature dendritic cells. Mature DCs loose the ability to take up antigen and the cells display up-regulated expression of co-stimulatory cell surface molecules and secrete various cytokines. Specifically, mature DCs express higher levels of MHC class I and II antigens and are generally identified as $CD80^+$, $CD83^+$, and $CD86^+$. Greater MHC expression leads to an increase in antigen density on the DC surface, while up regulation of co-stimulatory molecules CD80 and CD86 strengthens the T cell activation signal through the counterparts of the co-stimulatory molecules, such as CD28 on the T cells.

Mature dendritic cells can be prepared (i.e., matured) by contacting the immature dendritic cells that have been cultured in the presence of GM-CSF alone with effective amounts or concentrations of a dendritic cell maturation agent. Dendritic cell maturation agents can include, for example, BCG, IFNγ, LPS, TNFα, and the like. Effective amounts of BCG typically range from about $10^5$ to $10^7$ cfu per milliliter of tissue culture media. Effective amounts of IFNγ typically range from about 100-1000 U per milliliter of tissue culture media. Bacillus Calmette-Guerin (BCG) is an avirulent strain of *M. bovis*. As used herein, BCG refers to whole BCG as well as cell wall constituents, BCG-derived lipoarabidomannans, and other BCG components that are associated with induction of a type 2 immune response. BCG is optionally inactivated, such as heat-inactivated BCG, formalin-treated BCG, and the like.

The immature DCs are typically contacted with effective amounts of BCG and IFNγ for about one hour to about 48 hours. The immature dendritic cells can be cultured and matured in suitable maturation culture conditions. Suitable tissue culture media include AIM-V®, RPMI 1640, DMEM, X-VIVO 15®, and the like. The tissue culture media can be supplemented with amino acids, vitamins, cytokines, such as GM-CSF, divalent cations, and the like, to promote maturation of the cells. Typically about 500 units/ml of GM-CSF is used.

Maturation of dendritic cells can be monitored by methods known in the art for dendritic cells. Cell surface markers can be detected in assays familiar to the art, such as flow cytometry, immunohistochemistry, and the like. The cells can also be monitored for cytokine production (e.g., by ELISA, another immune assay, or by use of an oligonucleotide array). Mature DCs of the present invention also loose the ability to uptake antigen, which can be analyzed by uptake assays familiar to one of ordinary skill in the art.

Antigens

The mature, primed dendritic cells prepared by the methods of the present invention can present antigen to T cells. Mature, primed dendritic cells can be formed by contacting immature dendritic cells with a predetermined antigen either prior to or during maturation.

Suitable predetermined antigens for use in the present invention can include any antigen for which T-cell activation is desired. Such antigens can include, for example, bacterial cells, or other preparation comprising bacterial antigens, tumor specific or tumor associated antigens (e.g., whole tumor or cancer cells, a tumor cell lysate, tumor cell membrane preparations, isolated or partially isolated antigens from tumors, fusion proteins, liposomes, and the like), viral particles or other preparations comprising viral antigens, and any other antigen or fragment of an antigen, e.g., a peptide or polypeptide antigen. In certain embodiments, the antigen can be associated with prostate cancer, for example the antigen can be, but not limited to, prostate specific membrane antigen (PSMA), prostutic acid phosphatase (PAP), or prostate specific antigen (PSA). (See, e.g., Pepsidero et al., *Cancer Res.* 40:2428-32 (1980); McCormack et al., *Urology* 45:729-44 (1995).) The antigen can also be a bacterial cell, bacterial lysate, membrane fragment from a cellular lysate, or any other source known in the art. The antigen can be expressed or produced recombinantly, or even chemically synthesized. The recombinant antigen can also be expressed on the surface of a host cell (e.g., bacteria, yeast, insect, vertebrate or mammalian cells), can be present in a lysate, or can be purified from the lysate. Alternatively, the antigen can be encoded by nucleic acids which can be ribonucleoic acid (RNA) or deoxyribonucleic acid (DNA), that are purified or amplified from a tumor cell.

Antigen can also be present in a sample from a subject. For example, a tissue sample from a hyperproliferative or other condition in a subject can be used as a source of antigen. Such a sample can be obtained, for example, by biopsy or by surgical resection. Such an antigen can be used as a lysate or as an isolated preparation. Alternatively, a membrane preparation of cells from a subject (e.g., a cancer patient), or an established cell line also can be used as an antigen or source of antigen or nucleic acid encoding the antigen.

In an exemplary embodiment, a tumor cell lysate recovered from surgical specimens can be used as a source of antigen. For example, a sample of a cancer patient's own tumor, obtained at biopsy or at surgical resection, can be used directly to present antigen to dendritic cells or to provide a cell lysate or nucleic acids for antigen presentation. Alternatively, a membrane preparation of tumor cells of a cancer patient can be used. The tumor cell can be, for example, prostatic, lung, ovarian, colon, brain, melanoma, or any other type of tumor cell. A lysate and membrane preparation can be prepared from isolated tumor cells by methods known in the art.

In another exemplary embodiment, purified or semi-purified prostate specific membrane antigen (PSMA, also known as PSM antigen), which specifically reacts with monoclonal antibody 7E11-C.5, can be used as antigen. (See generally Horoszewicz et at, *Prog. Clin. Biol. Res.* 37:115-32 (1983), U.S. Pat. Nos. 5,162,504; 5,788,963; Feng et al., *Proc. Am. Assoc. Cancer Res.* 32:(Abs. 1418) 238 (1991); the disclosures of which are incorporated by reference herein.) In yet another exemplary embodiment, an antigenic peptide having the amino acid residue sequence Leu Leu His Glu Thr Asp Ser Ala Val (SEQ ID NO:1) (designated PSM-P1), which corresponds to amino acid residues 4-12 of PSMA, can be used as an antigen. Alternatively, an antigenic peptide having the amino acid residue sequence Ala Leu Phe Asp Ile Glu Ser Lys Val (SEQ ID NO: 2) (designated PSM-P2), which corresponds to amino acid residues 711-719 of PSMA, can be used as antigen.

In a particular embodiment, an antigenic peptide having an amino acid residue sequence Xaa Leu (or Met) Xaa Xaa Xaa Xaa Xaa Xaa Val (or Leu) (designated PSM-PX), where Xaa represents any amino acid residue, can be used as antigen. This peptide resembles the HLA-A0201 binding motif, i.e., a binding motif of 9-10 amino acid residues with "anchor residues", leucine and valine found in HLA-A2 patients. (See, e.g., Grey et al., *Cancer Surveys* 22:37-49 (1995).) This peptide can be used as antigen for HLA-A2 patients (see, Central Data Analysis Committee "Allele Frequencies", Section 6.3, Tsuji, K. et al. (eds.), Tokyo University Press, pp. 1066-1077). Similarly, peptides resembling other HLA binding motifs can be used.

Typically, immature dendritic cells obtained by the methods of the present invention are cultured in the presence of a dendritic cell maturation agent, such as, BCG, IFNγ, LPS, TNFα, or combinations thereof, and the predetermined antigen under suitable maturation conditions, as described above. Optionally, the immature dendritic cells can be admixed with the predetermined antigen in a typical dendritic cell culture media with or without GM-CSF, and/or a maturation agent. Following at least about 10 minutes to about 2 days of culture with the antigen, the antigen can be removed and culture media supplemented with BCG and IFNγ can be added. GM-CSF can also be added to the maturation media without additional cytokines, such as IL-4. Methods for contacting dendritic cells with antigen are generally known in the art. (See generally Steel and Nutman, *J. Immunol.* 160:351-60 (1998); Tao et al., *J. Immunol.* 158:4237-44 (1997); Dozmorov and Miller, *Cell Immunol.* 178:187-96 (1997); Inaba et al., *J Exp Med.* 166:182-94 (1987); Macatonia et al., *J Exp Med.* 169: 1255-64 (1989); De Bruijn et al., *Eur. J. Immunol.* 22:3013-20 (1992); the disclosures of which are incorporated by reference herein).

The resulting mature, primed dendritic cells are then co-incubated with T cells, such as naïve T cells. T cells, or a subset of T cells, can be obtained from various lymphoid tissues for use as responder cells. Such tissues include but are not limited to spleen, lymph nodes, and/or peripheral blood. The cells can be co-cultured with mature, primed dendritic cells as a mixed T cell population or as a purified T cell subset. T cell purification can be achieved by positive, or negative selection, including but not limited to, the use of antibodies directed to CD2, CD3, CD4, CD8, and the like.

By contacting T cells with mature, primed dendritic cells, antigen-reactive, or activated, polarized T cells or T lymphocytes are provided. As used herein, the term "polarized" refers to T cells that produce high levels of IFNγ or are otherwise primed for a type 1 (Th-1) response. Such methods typically include contacting dendritic cells with BCG and IFNγ to prepare mature, primed dendritic cells. The immature dendritic cells can be contacted with a predetermined antigen during or prior to maturation. The immature dendritic cells can be co-cultured with T cells (e.g., naïve T cells) during maturation, or co-cultured with T cells (e.g., naïve T cells) after maturation and priming of the dendritic cells for inducing a type 1 response. Further, the immature dendritic cells or mature dendritic cells can be partially purified, or enriched, prior to maturation. In addition, T cells can be enriched from a population of lymphocytes prior to contacting with the dendritic cells. In a specific embodiment, enriched or purl fed populations of $CD4^+$ T cells are contacted with the mature, primed dendritic cells. Co-culturing of mature, primed dendritic cells with T cells leads to the stimulation of specific T cells which mature into antigen-reactive $CD4^+$ T cells or antigen-reactive $CD8^+$ T cells.

In another aspect, methods are provided for re-stimulation of T cells in vitro, by culturing the cells in the presence of immature dendritic cells, or mature dendritic cells primed toward inducing a type 1 (Th-1) T cell response. Such T cell optionally can be cultured on feeder cells. The immature dendritic cells or the mature, primed dendritic cells optionally can be irradiated prior to contacting with the T cells. Suitable culture conditions can include one or more cytokines (e.g., purified IL-2, Concanavalin A-stimulated spleen cell supernatant, interleukin 15 (IL-15), and the like, as well as combinations thereof). Such in vitro re-stimulation of T cells can be used to promote expansion of the T cell populations.

A stable antigen-specific, polarized T cell culture or T cell line can be maintained in vitro for long periods of time by periodic re-stimulation. The T cell culture or T cell line thus created can be stored, and if preserved (e.g., by formulation with a cryopreservative and freezing) used to re-supply activated, polarized T cells at desired intervals for long term use.

In certain embodiments, activated $CD8^+$ or $CD4^+$ T cells can be generated according to the method of the present invention. Typically, mature, primed dendritic cells used to generate the antigen-reactive, polarized T cells are syngeneic to the subject to which they are to be administered (e.g., are obtained from the subject). Alternatively, dendritic cells having the same HLA haplotype as the intended recipient subject can be prepared in vitro using non-cancerous cells (e.g., normal cells) from an HLA-matched donor. In a specific embodiment, antigen-reactive T cells, including CTL and Th-1 cells, are expanded in vitro as a source of cells for treatment.

According to yet another aspect of the invention, non-activated monocytic dendritic precursor cells, immature dendritic cells, and mature primed dendritic cells can be preserved, e.g., by cryopreservation. Each population can be recovered prior to continuing with the processes described herein. For example, monocytic dendritic cell precursors can be obtained from a patient in the form of a leukapheresis or apheresis product prior to culture in a dendritic cell culture media in the presence of an adhesion blocking agent and GM-CSF to form and maintain immature dendritic cells. Subsequent to the preparation of immature dendritic cells these cells can be cryopreserved either before exposure to antigen and maturation or prior to administration to an individual to be treated. Cryopreservation agents which can be used include but are not limited to dimethyl sulfoxide (DMSO), glycerol, polyvinylpyrrolidone, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts. Different cryoprotective agents and different cell types typically have different optimal cooling rates. The heat of fusion phase where water turns to ice typically should be minimal. The cooling procedure can be carried out by use of, e.g., a programmable freezing device or a methanol bath procedure. Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, dendritic cells can be rapidly transferred to a long-term cryogenic storage vessel. In a typical embodiment, samples can be cryogenically stored in liquid nitrogen (−196° C.) or its vapor (−165° C.). Considerations and procedures for the manipulation, cryopreservation, and long term storage of hematopoietic stem cells, particularly from bone marrow or peripheral blood, is largely applicable to the non-activated dendritic cells of the present invention. A discussion of cryopreservation for hematopoietic stem cells can be found, for example, in the following references, incorporated by reference herein: Taylor et al., *Cryobiology* 27:269-78 (1990); Gorin, Clinics in *Haematology* 15:19-48 (1986); *Bone-Marrow Conservation, Culture and Transplantation, Proceedings of a Panel*, Moscow, Jul. 22-26, 1968, International Atomic Energy Agency, Vienna, pp. 107-186.

Frozen cells are typically thawed quickly (e.g., in a water bath maintained at 37-41° C.) and chilled immediately upon thawing. It may be desirable to treat the cells in order to prevent cellular clumping upon thawing. To prevent clumping, various procedures can be used, including but not limited to the addition before and/or after freezing of DNase (Spitzer et al., *Cancer* 45: 3075-85 (1980)), low molecular weight dextran and citrate, hydroxyethyl starch (Stiff et al., *Cryobiology* 20: 17-24 (1983)), and the like. The cryoprotective agent, if toxic in humans, should be removed prior to therapeutic use of the thawed low adherence dendritic cells. One way in which to remove the cryoprotective agent is by dilution to an insignificant concentration. Once frozen DC's have been thawed and recovered, they can be used to activate T cells as described herein with respect to non-frozen DC's.

In vivo Administration of Cell Populations

In another aspect of the invention, methods are provided for administration of mature, primed dendritic cells or activated, polarized T cells, or a cell population containing such cells, to a subject in need of immunostimulation. Such cell populations can include immature dendritic cells, partially matured dendritic cells, mature, primed dendritic cell populations and/or activated, polarized T cell populations. In certain embodiments, the methods are performed by obtaining non-activated dendritic cell precursors or immature dendritic cells, differentiating those cells with GM-CSF in the absence of additional cytokines, and maturing those cells in the presence of a maturation agent, such as for example, BCG, and/or IFNγ and predetermined antigen to form a mature dendritic cell population primed towards Th-1 response. The immature dendritic cells can be contacted with antigen prior to or during maturation. Such mature, primed dendritic cells can be administered directly to a subject in need of immunostimulation.

In a related embodiment, the mature, primed dendritic cells can be contacted with lymphocytes from a subject to stimulate T cells within the lymphocyte population. The activated, polarized lymphocytes, optionally followed by clonal expansion in cell culture of antigen-reactive $CD4^+$ and/or $CD8^+$ T cells, can be administered to a subject in need of immunostimulation. In certain embodiments, activated, polarized T cells are autologous to the subject.

In another embodiment, the dendritic cells, T cells, and the recipient subject have the same MHC (HLA) haplotype. Methods of determining the HLA haplotype of a subject are known in the art. In a related embodiment, the dendritic cells and/or T cells are allogenic to the recipient subject. For example, the dendritic cells can be allogenic to the T cells and the recipient, which have the same MHC (HLA) haplotype. The allogenic cells are typically matched for at least one MHC allele (e.g., sharing at least one but not all MHC alleles). In a less typical embodiment, the dendritic cells, T cells and the recipient subject are all allogeneic with respect to each other, but all have at least one common MHC allele in common.

According to one embodiment, the T cells are obtained from the same subject from which the immature dendritic cells were obtained. After maturation and polarization in vitro, the autologous T cells are administered to the subject to provoke and/or augment an existing immune response. For example, T cells can be administered, by intravenous infusion, for example, at doses of about $10^8$-$10^9$ cells/m² of body surface area (see, e.g., Ridell et al., Science 257:238-41 (1992), incorporated herein by reference). Infusion can be repeated at desired intervals, for example, monthly. Recipients can be monitored during and after T cell infusions for any evidence of adverse effects.

According to another embodiment, dendritic cells obtained by the process described in the present application are grown only in the presence of GM-CSF, matured with BCG and IFNγ, and according to the present invention can be injected directly into a tumor, the region surrounding a tumor, or other tissue containing a target antigen. Such mature cells can take up antigen and present that antigen to T cells in vivo.

The following examples are provided merely as illustrative of various aspects of the invention and shall not be construed to limit the invention in any way.

Example 1

In this example it was demonstrated that in vitro differentiation of monocytes into $CD1a^+$ dendritic cells in the presence of GM-CSF alone requires that the cells not be allowed to form an initial adherence to a culture vessel.

Briefly, $CD14^+CD1a^-$ monocytes were resuspended in either Iscove-modified Dulbecco's medium (IMDM, BioWhittaker) plus 2 mM L-glutamine (Gibco BRL) or X-VIVO-15® (BioWhittaker) plus 3% human serum albumin (HSA, Bayer). Cell suspensions were transferred into T-25 culture flasks (Greiner) and incubated for 30 minutes in a 6% $CO_2$, 37° C. incubator. After the incubation, human serum albumin (HSA) and granulocyte-macrophage colony-stimulating factor (GM-CSF, Immunex) were added to achieve a final concentration of 3% HSA and 500 units/ml GM-CSF. Both cultures were incubated for 4 days in a 6% $CO_2$, 37° C. incubator. The surface expression of CD14 and CD1a were analyzed by use of labeled monoclonal antibodies specific for the molecules and detection using flow cytometry. Dotted histograms represented isotype control (background) staining (FIG. 1).

Cells, monocytes initially incubated in media with no HSA showed tight adherence to plastic as determined by phase contrast microscopy, as evidenced by flattening out of the cells on the surface, while those incubated in media with HSA showed a decreased extent of adhesion. This was evidenced by the spherical shape of the cells as determined by phase contrast microscopy. After 4 days in culture, the former culture retained some CD14 expression and expressed very low levels of CD1a. (FIG. 1). In contrast, a majority of cells not allowed to adhere tightly to the surface of the culture vessel were $CD14^-$ and $CD1a^+$ characteristic of immature dendritic cells.

In another example, it was demonstrated that monocytes would differentiate in vitro into $CD1a^+$ dendritic cells in the presence of GM-CSF alone when the cells were not allowed to form an adherence to a Teflon® culture bag.

Figure 2A:
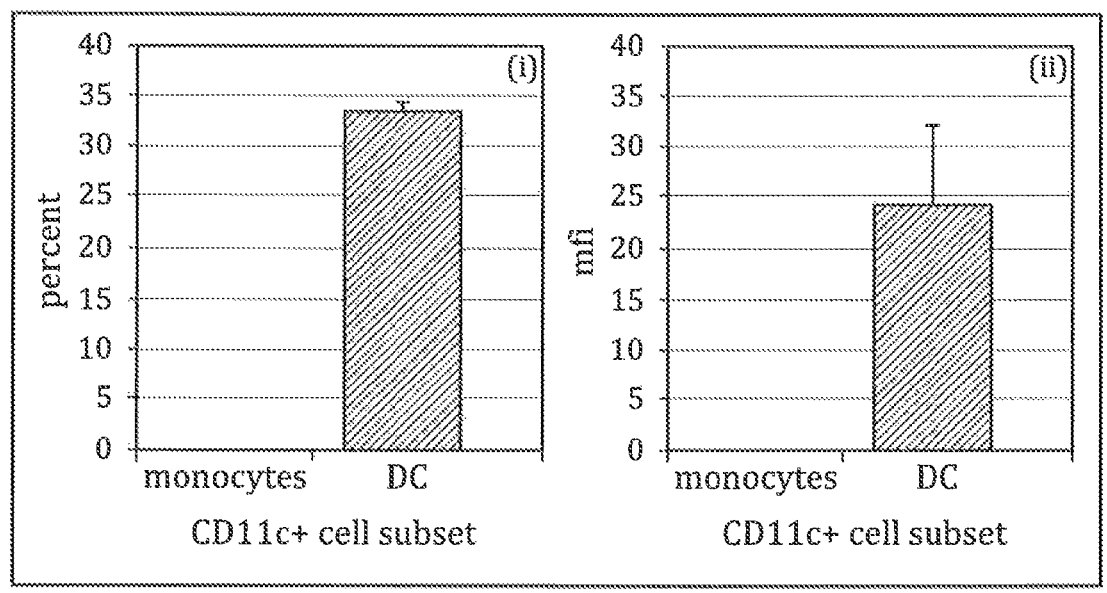
FIG. 2A demonstrates the up regulation of CD1a on day 5 DC relative its expression on the surface of precursor monocytes.
Figure 2B:
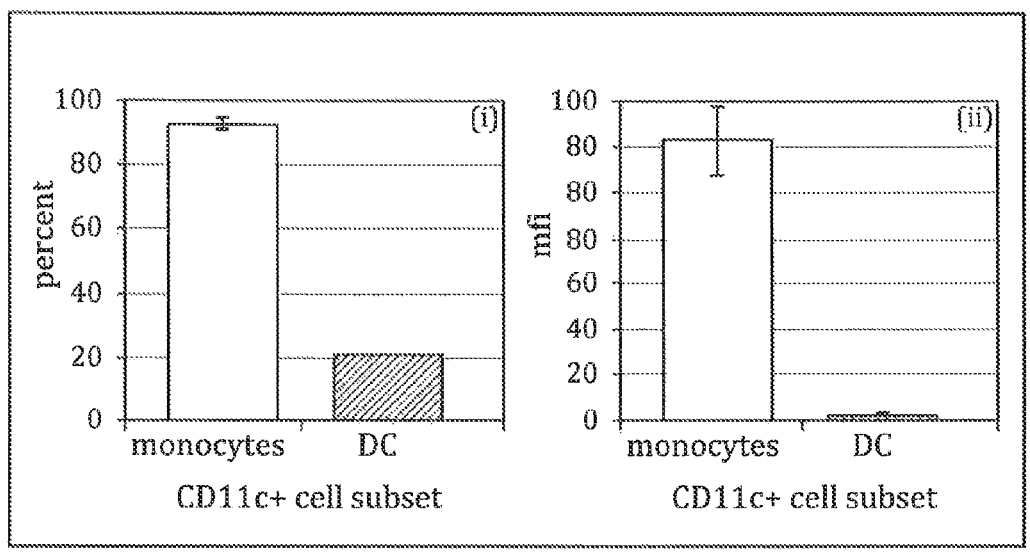
FIG. 2B demonstrates the down-regulation of the expression of CD14 on DCs relative to its level on the precursor monocytes. Data are shown for the respective cultures after electronic gating on cells of the monocyte lineage (CD11c$^+$) for (i) subsets and (ii) relative expression as measured by mean fluorescence intensity (mfi). Background staining observed with the relevant isotype control antibodies has been subtracted. These data represent the averages from monocytes isolated and cultured from two independent donors.

Briefly, isolated monocytes from two leukapheresis donors, were independently resuspended in X-VIVO-15® (BioWhittaker) plus granulocyte-macrophage colony-stimulating factor (GM-CSF, Immunex) and human serum albumin (HSA, Plasburnin™, Bayer) to achieve a final concentration 500 units/ml GM-CSF and 2% HSA, in the Teflon® bags. Cell suspensions in the bags were transferred to a 6% $CO_2$, 37° C. incubator for 5 days. At the conclusion of the culture period, maturation agents (1:400 dilution of inactivated BCG (Organon-Teknika) and 500 U/ml IFN-γ (R and D Systems)) were added to the cultures. The maturation event was allowed to proceed for 4 hours. The surface expression of CD14 and CD1a on "live" cells was analyzed after forward-scatter (FS) and side-scatter (SS) gating with labeled monoclonal antibodies specific for the molecules using fluorescent activated cell flow analysis (FIGS. 2A and 2B). Isotype control antibodies were used as controls for background fluorescence and were $IgG_1$ for the antibody specific for CD1a and $TgG_{2b}$ for the antibody specific for CD14.

Precursor cells initially isolated expressed high levels of CD14 and expressed very low levels or no CD1a typical of monocytes. (FIGS. 2A and 2B). In contrast, a majority of cells post-low adherence culture were $CD14^-$ and $CD1a^+$ as would be expected of monocyte derived dendritic cells.

Example 2

In this example immature dendritic cells derived from monocytes that had not been allowed to adhere to the surface of the culture vessel were matured and tested for the secretion of IL-12. The amount of IL-12 secreted from the dendritic cells was compared to mature dendritic cells isolated by typical methods and cultured in the presence of GM-CSF and IL-4.

Figure 3:
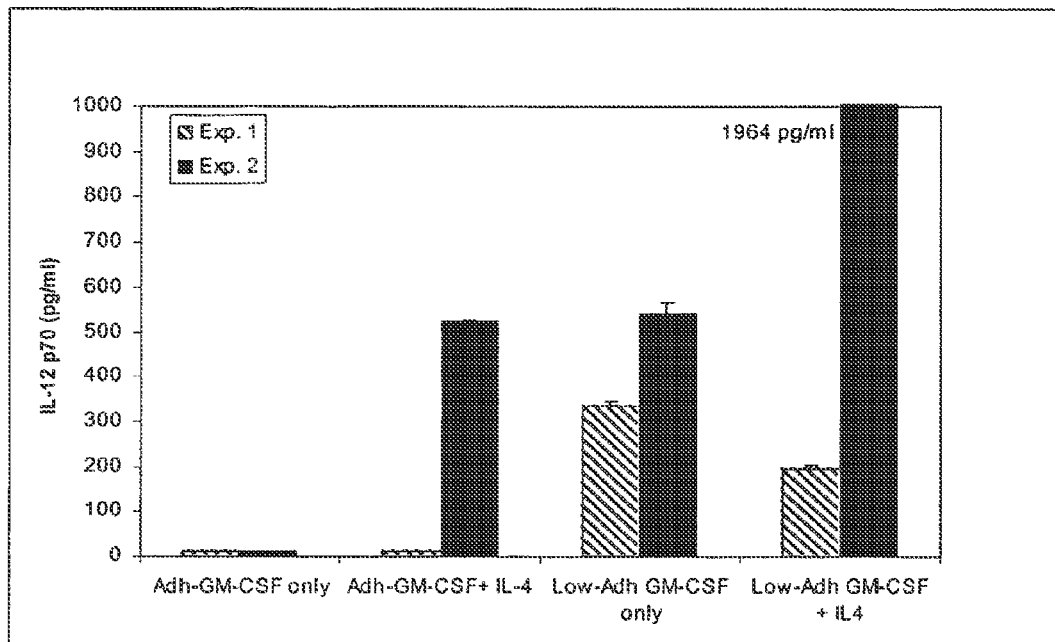
FIG. 3 depicts the quantitation of IL-12 p70 secretion from monocytic dendritic cell precursors that have been allowed to tightly adhere or loosely adhere to a substrate prior to culture in either GM-CSF and IL-4 or GM-CSF alone.

Briefly, cryopreserved monocytes were resuspended at a concentration of $1\times10^6$ cells/ml in Iscove modified Dulbecco's media (IMDM, BioWhittaker) plus 2 mM L-Glutamine (Gibco BRL) in the absence or presence of 3% human serum albumin (HSA, Bayer). The cell suspension was transferred into two tissue culture flasks (Greiner) per condition, and cultured for 30 minutes in a 6% $CO_2$, 37° C. humidified incubator. After the incubation period, HSA was added to achieve a final concentration of 3% HSA in all flasks. Granulocyte-macrophage colony stimulating factor (GM-CSF, Immunex) or GM-CSF and interleukins-4 (IL-4, R & D Systems) were added to each culture condition at a final concentration of 500 units/ml. All cultures were incubated for 30 minutes in a 6% $CO_2$, 37° C. humidified incubator for 4 days. At the conclusion of the culture period, maturation agents (1:400 dilution of inactivated Bacillus Calmette-Guerrin (BCG, Organon-Teknika) and 500 U/ml interferon-γ (IFN-γ, R and D Systems)) were added to the flask. Maturation was allowed to proceed for 18-24 hours. Culture supernatants were collected and assayed for IL-12 p70 secretion. Results from two separate experiments were compared. In both experiments, IL-12 p70 secretions were detected in cultures supplemented with GM-CSF alone or GM-CSF and IL-4. (FIG. 3). In addition, monocytes subjected to tight initial adherence, followed by culture in GM-CSF alone, failed to secrete IL-12 p70 in both experiments. In one experiment, IL-12 p70 secretion was detected in a culture subjected to tight initial adherence, followed by a 4 day culture in the presence of GM-CSF and IL-4.

Example 3

In this example the expression of cell surface markers typical of dendritic cells were assayed in non-activated monocytes cultured in the presence of GM-CSF alone. Non-activated monocytes cultured in GM-CSF alone demonstrated the expression of cell surface markers typical of mature DCs.

Figure 4:
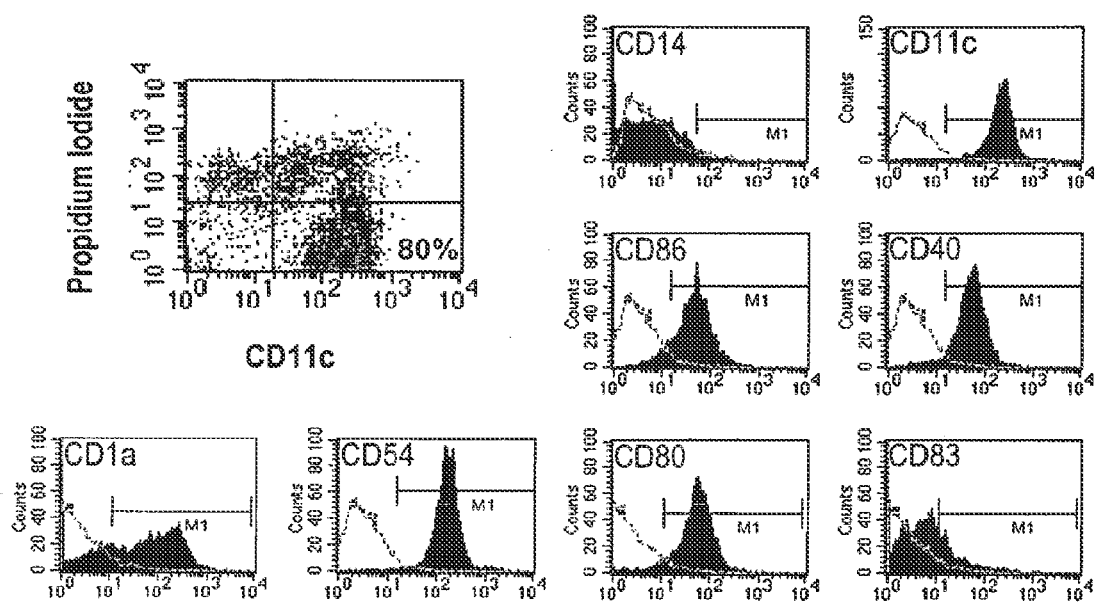
FIG. 4 depicts the expression of typical dendritic cell markers for monocytic dendritic precursor cells cultured in GM-CSF alone.

Briefly, cryopreserved monocytes were resuspended at a concentration of $1 \times 10^6$ cells/ml in DC culture media containing X-VIVO-15® (BioWhittaker), 2% human serum albumin (Bayer), and 500 U/ml GM-CSF (Immunex). The cell suspension was transferred into a tissue culture flask (Greiner), and cultured for 4 days in a 6% $CO_2$, 37° C. humidified incubator. At the conclusion of the culture period, maturation agents (1:400 dilution of inactivated BCG (Organon-Teknika) and 500 U/ml IFN-γ (R and D Systems)) were added to the flask. The maturation event was allowed to proceed for 18-24 hours. Matured DCs were harvested and characterized. The cells were reacted with labeled monoclonal antibodies specific for CD11c, CD1a, CD40, CD80, CD86, CD54, and CD83. In addition, the cells were stained with propidium iodide. Label was detected by flow cytometry. These data demonstrated that 80% of the cells recovered were live DCs ($CD11c^+$ and propidium iodide$^-$). In addition, these cells express typical DC markers, i.e., a lack of CD14 expression, and expression of CD11c, CD1a, CD40, CD80, CD86, CD54, and CD83. (FIG. 4).

Example 4

In this example monocytic dendritic precursor cells that were cultured in the presence of a adhesion blocking agent were tested for the kinetics of in vitro differentiation into dendritic cells in medium supplemented with GM-CSF alone.

Briefly, cryopreserved monocytes were resuspended at a concentration of $1 \times 10^6$ cells/ml in DC culture media containing X-VIVO-15® (BioWhittaker), 2% human serum albumin (Bayer), and 500 U/ml GM-CSF (Immunex). The cell suspension was transferred into a Teflon® bag (Americal Fluoroseal), and cultured for 5 days in a 6% $CO_2$, 37° C. humidified incubator. On day 5, maturation agents (1:400 dilution of inactivated BCG (Organon-Teknika) and 500 U/ml IFNγ (R and D Systems)) were added to the culture bag. The maturation event was allowed to proceed for about 18 hours. Cells were harvested daily from the bag for flow cytometric analyses of the expression of CD14 and CD1a. Data from these analyses demonstrated that the conversion from monocytes ($CD14^+$ and $CD1a^-$) to DCs ($CD14^-$, $CD1a^+$) started between 1 and 2 days after the start of the culture. (FIG. 5). By day 3, phenotype conversions were completed.

Example 5

In this example the phenotype of DCs cultured in either Teflon bags or in flasks under various culture conditions were compared. The cells were grown in either GM-CSF alone or in GM-CSF supplemented with IL-4. A comparison was also made of the phenotype of cells that had or had not been exposed to maturation agents.

Briefly, monocytes were resuspended at $1 \times 10^6$ cells/ml in X-VIVO-15® (BioWhittaker) and 2% HSA (Bayer) supplemented with 500 U/ml GM-CSF alone, or in GM-CSF in combination with 500 U/ml IL-4. Cell suspensions (duplicate bags for each culture conditions) were cultured in Teflon bags (American Fluoroseal), or tissue culture flasks (GM-CSF/IL-4 combination only) in a 6% $CO_2$, 37° C. incubator. After 5 days, maturation agents (1:400 dilution of inactivated BCG (Organon-Teknika) and 500 U/ml IFN-γ (R and D Systems)) were added to one of the duplicate Teflon bag cultures, as well as the flask culture. On day 6, all cultures were harvested. Their phenotypes were analyzed using staining with labeled monoclonal antibodies specific for CD80, CD83, CD86 and HLA-DR with detection by flow cytometry.

Figure 6A:
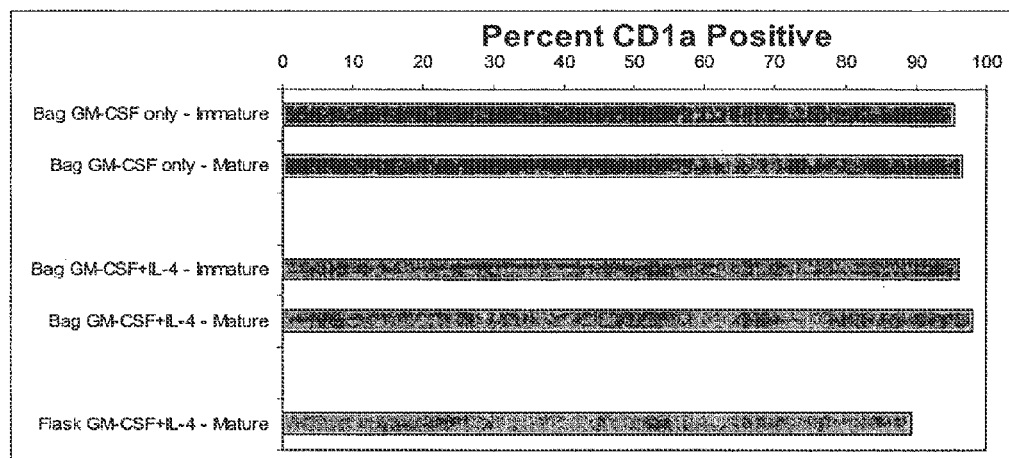
FIGS. 6A through 6E depict a phenotype comparison of non-activated monocytes into dendritic cells cultured in either Teflon® bags or plastic tissue culture flasks in cell culture media supplemented with GM-CSF alone or GM-CSF plus IL-4 in the presence or absence of a dendritic cell maturation factor.
Figure 6B:
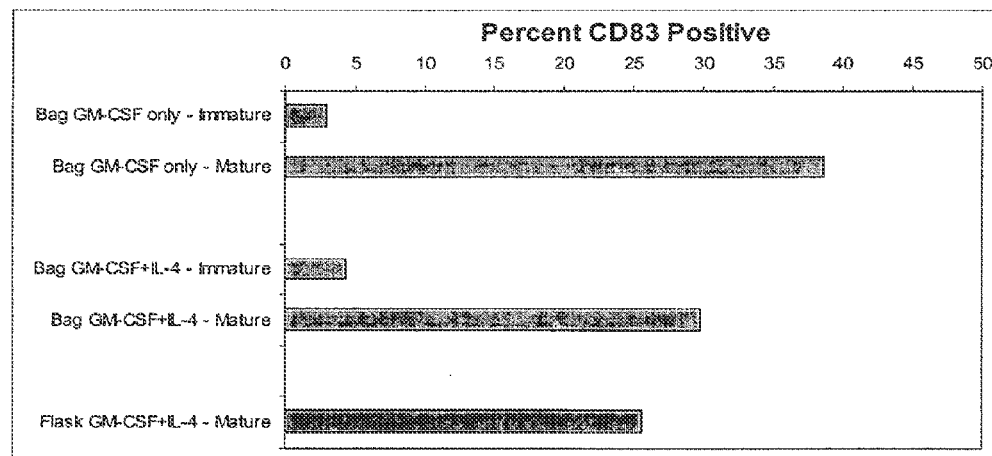
Figure 6C:
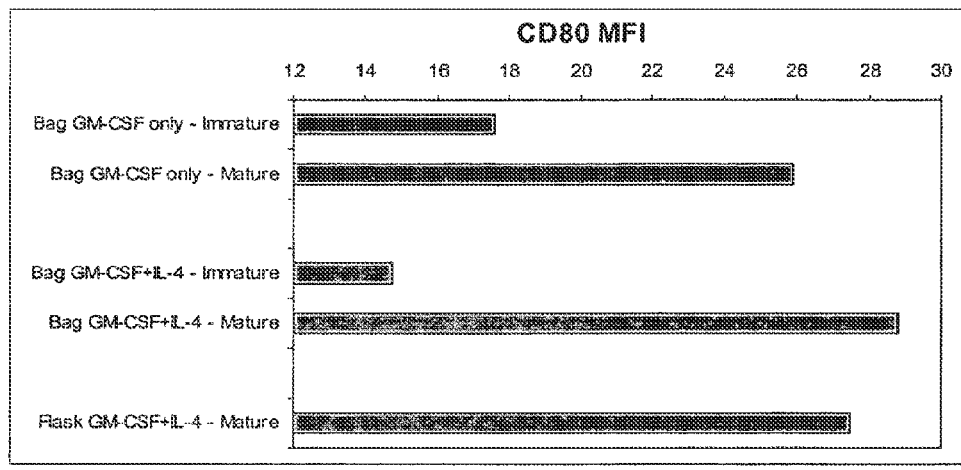
Figure 6D:
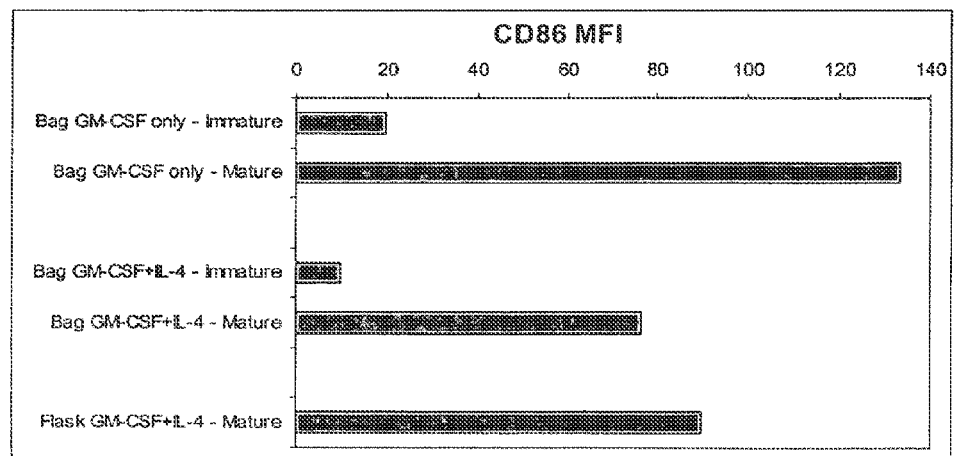
Figure 6E:
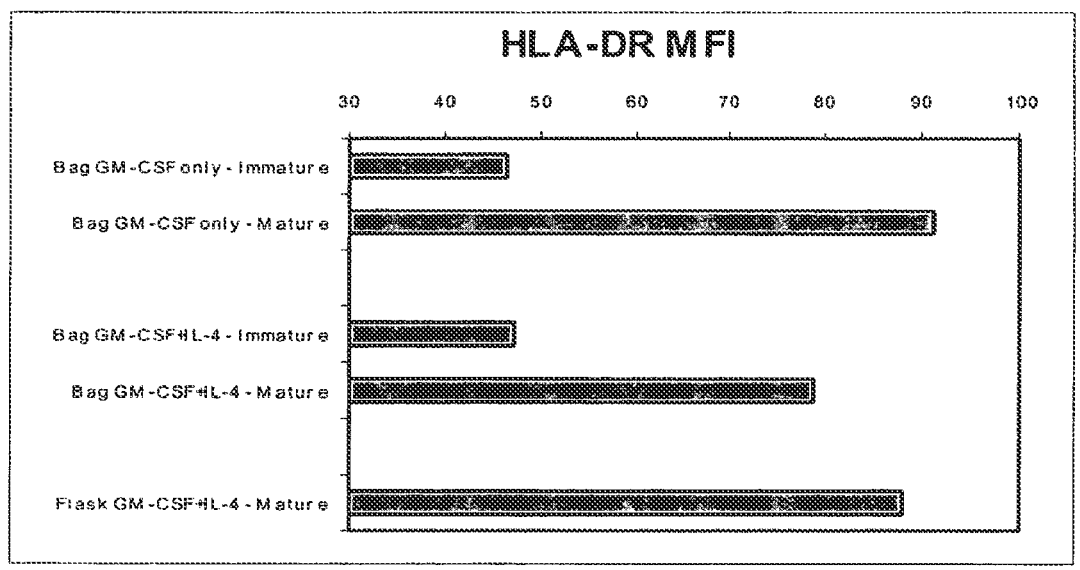

Most of the DCs from all five culture conditions expressed CD1a (89-97%). (FIG. 6A). In both GM-CSF and GM-CSF/IL-4 cultures, significant expression of the DC maturation marker, CD83, (FIG. 6B) was observed only in cultures exposed to the maturation agents. In addition, a significant increase in the surface expression of co-stimulatory molecules (CD80 and CD86, FIGS. 6C and 6D), as well as HLA-DR (FIG. 6E) was observed, as these DCs had matured. The levels of expression of these molecules were similar in all three mature DC populations.

In addition, the T cell stimulatory functions of DCs generated from monocytes subjected to an initial tight adherence step were compared to DCs generated in the absence of tight adherence in the presence of an adhesion blocking agent. In this study, two sources of monocytes were used as starting populations. For the tight adherent monocyte population, peripheral blood mononuclear cells (PBMCs) were incubated in OPTIMEM-1 (Gibco BRL) plus 1% heat-inactivated autologous plasma for 1 hour in a tissue culture flask (Greiner). After the incubation, non-adherent cells were removed, leaving an enriched adherent activated monocyte population on the surface of the flask. To obtain the non-activated monocyte population, monocytes were obtained from a column containing human-serum albumin (HSA) coated glass microcarrier beads (bead box).

Each of the populations of monocytes, activated and non-activated were then incubated in X-VIVO-15® with 2% HSA in the presence of GM-CSF alone or in combination with IL-4 for 5 days. The resulting immature DCs were loaded with influenza A M1-A4 40mer peptide or keyhole limpet hemocyanin (KLH) for one hour prior to washing and maturing with BCG (1:400 dil) and IFN-γ (500 U/mL). After harvesting and washing the mature DC, co-cultures with DCs and autologous PBMCs were set up at a 1:10 DC:PBMC ratio in ATM-Vi plus 5% human AB sera (HuAB Sera) supplemented with 20 ng/ml IL-2 from day 2 through day 8. After eight days of culture the T cell lines were harvested and analyzed for M1-A4 specific CD8 T cell expansion (Vβ17+ CD8+ T cells) by flow cytometry.

Figure 7A:
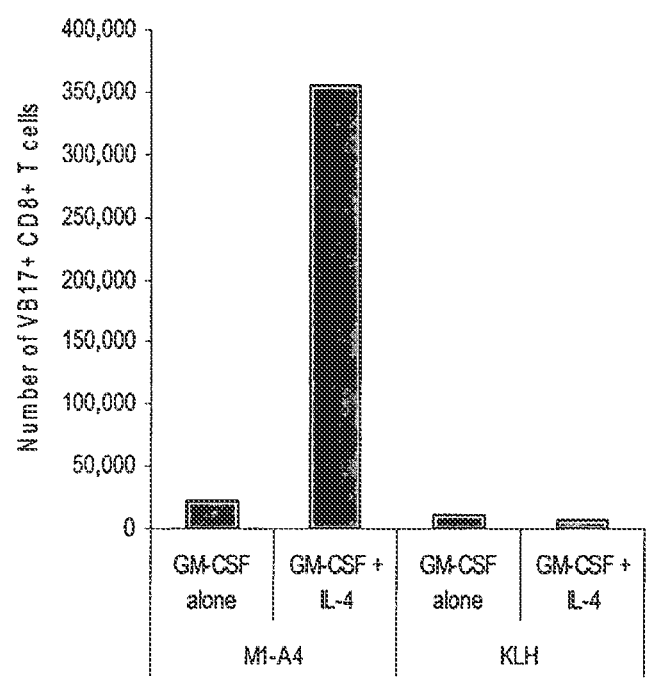
FIGS. 7A and 7B depict the antigen specific T cell response of dendritic cells generated by adherence to glass covered micro-carrier beads, cultured in the presence of either GM-CSF alone or GM-CSF and IL-4, and subsequently contacted with either a control antigen keyhole limpet hemocyanin or influenza A M1-A4 40 mer peptide and a dendritic cell maturation agent.
Figure 7B:
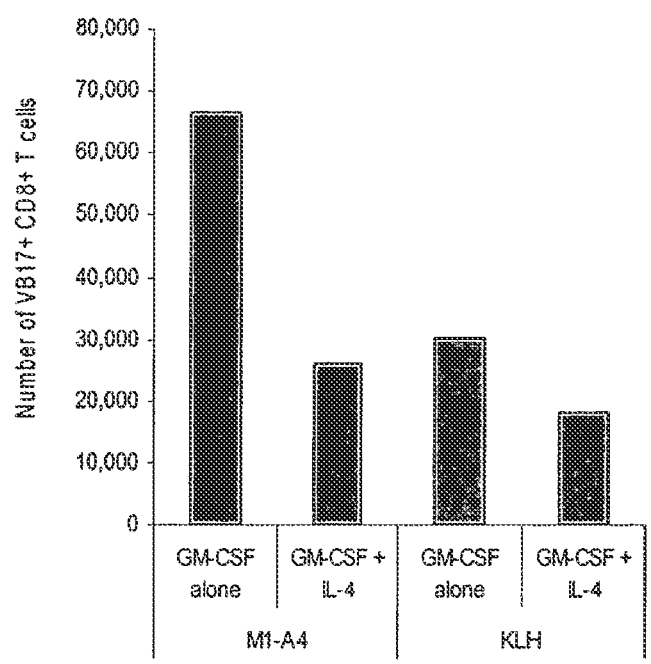

Compared to the KLH controls, DCs generated by adherence to plastic require IL-4 to generate an influenza (M1-A4) specific response. (FIG. 7A). However DCs generated from bead box isolated monocytes (non-activated) are most efficient at initiating a secondary CD8 T cell response when GM-CSF alone was used during their generation. (FIG. 7B).

Example 6

In this example the expression of cell surface markers typical of dendritic cells were assayed in non-activated monocytes that had been enriched by tangential flow filtration and cultured in the presence of GM-CSF alone. Dendritic cells cultured in GM-CSF alone demonstrated the expression of cell surface markers typical of maturing DCs.

Figure 8A:
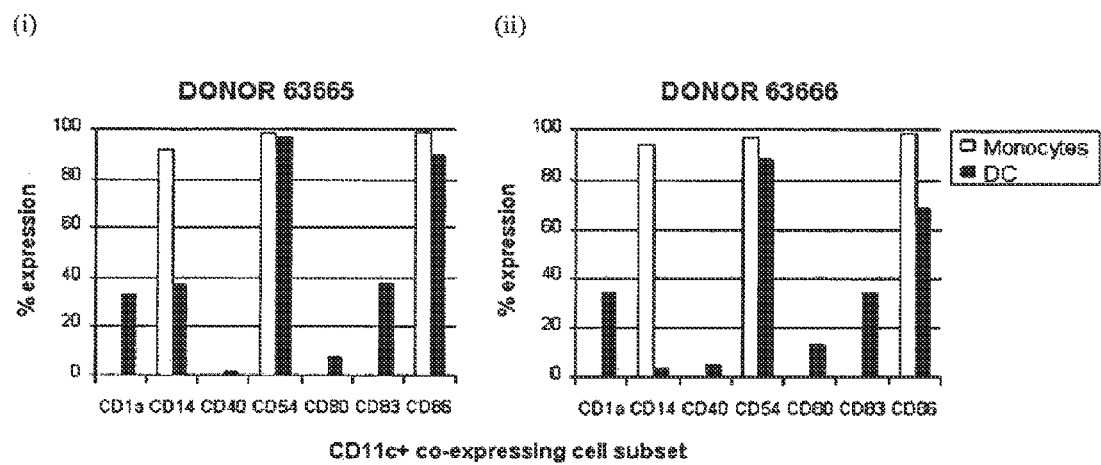
FIGS. 8A and 8B depict the phenotypic profiles on cells of monocytic lineage that have differentiated to dendritic cells (DC) following in vitro culture in the absence of IL-4. Markers on all subsets and their relative levels of expression (mfi) are shown on "live" CD11c$^+$ cells.
Figure 8B:
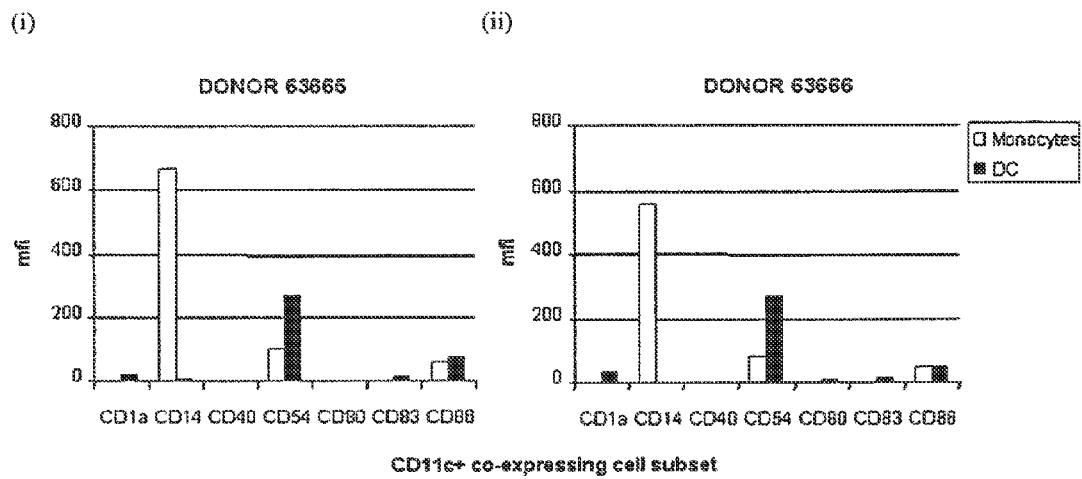

Briefly, cryopreserved monocytes previously isolated via a tangential flow filtration process from two different blood donors. This process comprised TFF of a sample of monocytes in a device having a filter with a pore size of 5.5 micron. The recirculation (input) rate was about 1400 ml/min, the filtration rate was about 17 ml/min, and the time was about 90 min. The enriched monocytic dendritic cell precursors were independently cultured at a concentration of $1 \times 10^6$ cells/mil in DC culture media containing X-VIVO-15 (BioWhittaker), 2% human serum albumin (Bayer), and 500 U/ml GM-CSF (Immunex). Cell suspensions in Teflon® bags were cultured for 5 days in a 6% $CO_2$, 37° C. humidified incubator. At the conclusion of the culture period, maturation agents (1:400 dilution of inactivated BCG (Organon-Teknika) and 500 U/ml IFN-γ (R and D Systems) were added to the cultures. The maturation event was allowed to proceed for 4 hours. Maturing DCs were harvested and characterized. The cells were reacted with labeled monoclonal antibodies specific for CD11c, CD1a, CD40, CD54, CD80, CD86, and CD83. Marker expression on "live" cells were analyzed by use of forward-scatter (FS) and side-scatter (SS) gating and with labeled monoclonal antibodies specific for the molecules and detection using flow cytometry. In addition, the cells were stained with propidium iodide. Label was detected by flow cytometry. Greater than 80% of the cells recovered were of the monocyte lineage, that is CD11c expressing and were "live" DCs (propidium iodide⁻, not shown). Significantly cells differentiated in the absence of IL4 express the typical DC markers, i.e., a decreased CD14 expression, and expression of CD1a, CD40, CD80, CD86, CD54, and CD83 (FIGS. 8A and 8B). Background fluorescence was measured using isotype control antibodies and were $IgG_1$, with the exception of CD14, where the isotype control was an $IgG_{2b}$ antibody.

Example 7

In this example it was determined that monocytes that were exposed to plastic surfaces (i.e., a tissue culture flask) became activated, unless tight interaction was blocked by the addition of a blocking agent, like human serum albumin (HAS).

Monocytes ($1 \times 10^6$/ml) were plated in tissue culture flasks in Iscove's modification of Dulbecco's Media (IMDM), with or without 3% (w/v) HSA, for 1 hour. After the 1 hour incubation at 37° C., 3% HSA was also added to the culture that was initially plated in the absence of HSA, and both cultures were incubated overnight at 37° C. The supernatants were then harvested, and levels of various cytokines that are typically associated with monocyte activation were measured. The cytokine concentrations (ng/ml) are shown in Table 1 below.

TABLE 1

| Cytokine | No HSA | 3% HSA |
|---|---|---|
| Interleukin 8 | 7,192 | 710 |
| Interleukin 6 | 752 | 200 |
| TNF-alpha | 44 | <5 |

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A method for differentiating human monocytic dendritic cell precursors (CD14$^+$CD1a$^-$) into immature dendritic cells having increased CD1a and having no CD14 on their cell surface, comprising:
   a) providing a cell population comprising non-activated human monocytic dendritic cell precursors (CD 14$^+$CD1a$^-$);
   b) contacting the non-activated human dendritic cell precursors in a culture vessel with a dendritic cell culture media supplemented with at least 1% animal or human protein and an effective amount of granulocyte-macrophage colony stimulating factor in the absence of additional cytokines for a time period sufficient for the human monocytic dendritic cell precursors to differentiate into immature dendritic cells having no expression of CD14 and having increased expression of CD1a on their cell surface.

2. The method according to claim 1, wherein the animal or human protein is an albumin, serum, plasma, gelatin, or polyamino acid.

3. The method according to claim 2, wherein the protein is human serum albumin.

4. The method according to claim 3, wherein the human serum albumin is present at a concentration of at least 1%.

5. The method according to claim 4, wherein the human serum albumin is present at a concentration of about 2% to about 10%.

6. The method according to claim 3, further comprising cryopreservation of the dendritic cells.

7. The method according to claim 1, wherein the dendritic cell culture medium is a serum free medium.

8. The method according to claim 1, wherein the cell population comprises peripheral blood, a leukapheresis product, an apheresis product, cord blood, spleen, lymph node, thymus, or bone marrow.

9. The method according to claim 8, wherein the cell population has been cryopreserved.

10. The method according to claim 8, wherein the dendritic cell precursors are further enriched by tangential flow filtration.

11. The method according to claim 10, wherein the tangential flow filtration is carried out in a device having a filter with a pore size of 5.5 microns, a recirculation (input) rate of 1400 ml/min, a filtration rate of 17 ml/min, and a filtration time of 90 min.

12. The method according to claim 1, wherein the culture vessel comprises polystyrene, glass coated polystyrene, styrene or glass.

13. The method according to claim 1, further comprising contacting the differentiated dendritic cell precursors with an antigen of interest for a time period sufficient for antigen uptake.

14. The method according to claim 13, further comprising contacting the differentiated dendritic cell precursors with a dendritic cell maturation agent.

15. The method according to claim 14, wherein the dendritic cell maturation agent comprises Bacillus Calmette-Guerin (BCG), lipopolysaccharide (LPS), TNFα, Interferon gamma (IFNγ), or combinations thereof.

16. The method according to claim 15, wherein the maturation agent is a combination of BCG and IFNγ.

17. The method according to claim 13, wherein the antigen is a tumor specific antigen, a tumor associated antigen, a viral antigen, a bacterial antigen, tumor cells, a nucleic acid encoding the antigen isolated from a tumor cell, bacterial cells, recombinant cells expressing an antigen, a cell lysate, a membrane preparation, a recombinantly produced antigen, a peptide antigen, or an isolated antigen.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Peptide antigen

<400> SEQUENCE: 1

Leu Leu His Glu Thr Asp Ser Ala Val
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide antigen

<400> SEQUENCE: 2

Ala Leu Phe Asp Ile Glu Ser Lys Val
1               5

```
<210> SEQ ID NO 3
<211> LENGTH: 9
<212> TYPE: PRT
<213> ORGANISM: Artificial Sequence
<220> FEATURE:
<223> OTHER INFORMATION: Peptide antigen
<220> FEATURE:
<221> NAME/KEY: MISC_FEATURE
<222> LOCATION: (1)..(1)
<223> OTHER INFORMATION: Xaa can be any occurring amino acid
<220> FEATURE:
<221> NAME/KEY: MISC_FEATURE
<222> LOCATION: (2)..(2)
<223> OTHER INFORMATION: Xaa can be Leu or Met
<220> FEATURE:
<221> NAME/KEY: MISC_FEATURE
<222> LOCATION: (3)..(8)
<223> OTHER INFORMATION: Xaa can be any occurring amino acid
<220> FEATURE:
<221> NAME/KEY: MISC_FEATURE
<222> LOCATION: (9)..(9)
<223> OTHER INFORMATION: Xaa can be Val or Leu

<400> SEQUENCE: 3

Xaa Xaa Xaa Xaa Xaa Xaa Xaa Xaa Xaa
1               5
```